United States Patent
Raschbaum

(10) Patent No.: US 6,432,083 B1
(45) Date of Patent: Aug. 13, 2002

(54) MECHANISM AND METHOD FOR MONITORING DUAL LUMEN BODY FLUID SUCTION SYSTEM

(75) Inventor: George R. Raschbaum, El Paso, TX (US)

(73) Assignee: MEDevices, Inc., Gurnee, IL (US)

( * ) Notice: Subject to any disclaimer, the term of this patent is extended or adjusted under 35 U.S.C. 154(b) by 0 days.

(21) Appl. No.: 09/410,418

(22) Filed: Jan. 1, 1999

(51) Int. Cl.⁷ .................................................. A61M 1/00
(52) U.S. Cl. ........................................................ 604/118
(58) Field of Search ................................. 604/118, 119, 604/318–321, 27, 35, 43, 45, 93.01, 246, 247

(56) References Cited

U.S. PATENT DOCUMENTS

| | | | | |
|---|---|---|---|---|
| 4,648,384 A | * | 3/1987 | Schmukler | 128/1 |
| 4,650,477 A | * | 3/1987 | Johnson | 604/321 |
| 4,735,606 A | * | 4/1988 | Davison | 604/28 |

* cited by examiner

*Primary Examiner*—Anhtuan T. Nguyen
*Assistant Examiner*—Ann Y Lam
(74) *Attorney, Agent, or Firm*—Charles F. Lind

(57) ABSTRACT

The invention is characterized by a sealed vessel defining a chamber that is partially filled with a liquid, preferably transparent and safe such as water. The vessel has an inlet for atmospheric air that via a tube is extended to open into the vessel under and into the vessel liquid, and an outlet that is located above the vessel liquid. The vessel outlet is connected to the inlet of the makeup air lumen of a dual lumen medical drainage tube. Negative pressure of a functioning suction/collection system applied to the suction lumen of the dual lumen tube thereby is linked via the makeup air lumen to the vessel chamber, and the resulting flow of makeup atmospheric air is as visible bubbles rising through the vessel liquid. The continuity of the bubble pattern through the vessel liquid thus offers assurance of non-changing air flow rate and assurance of proper functioning of the dual lumen drainage tube.

8 Claims, 2 Drawing Sheets

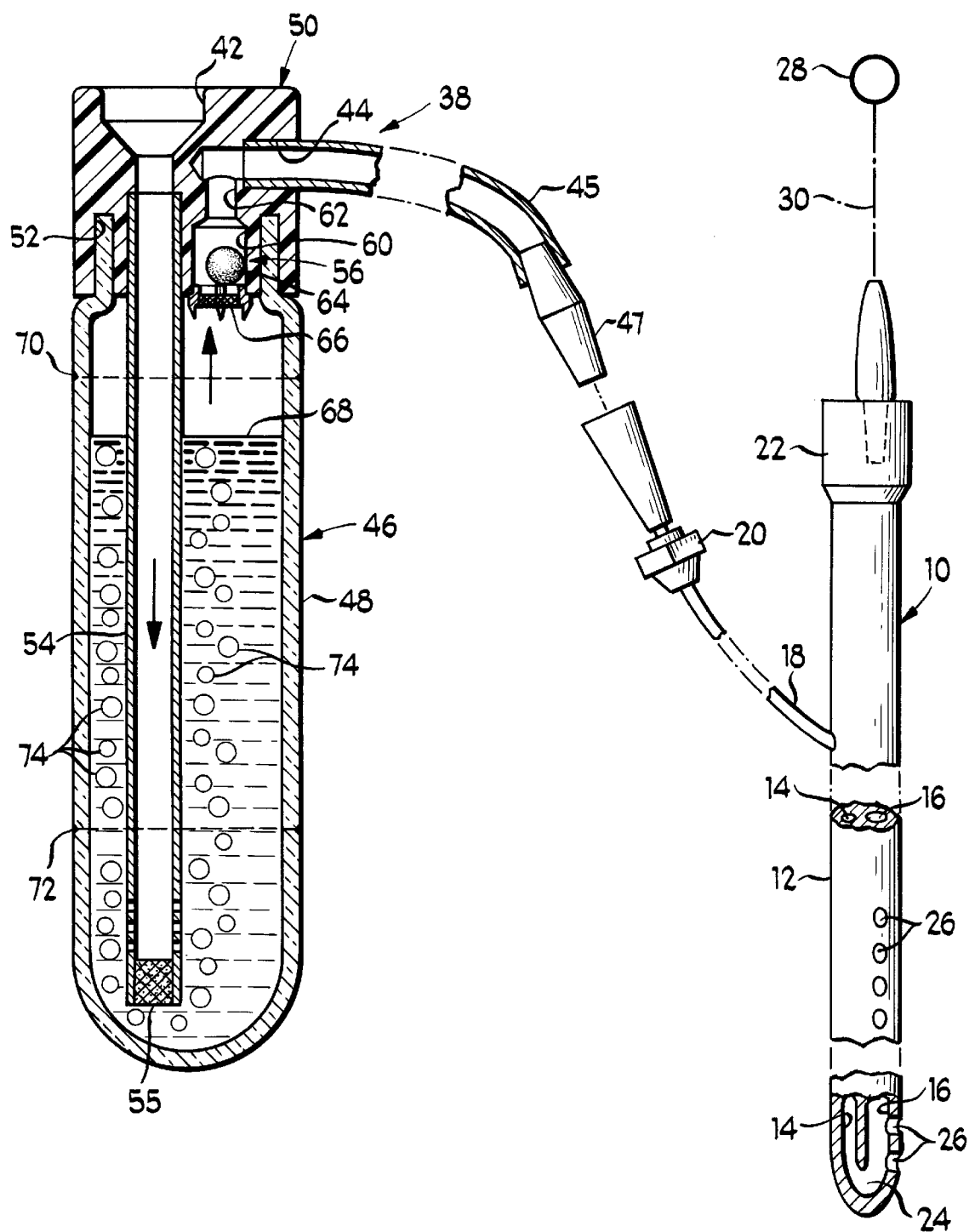

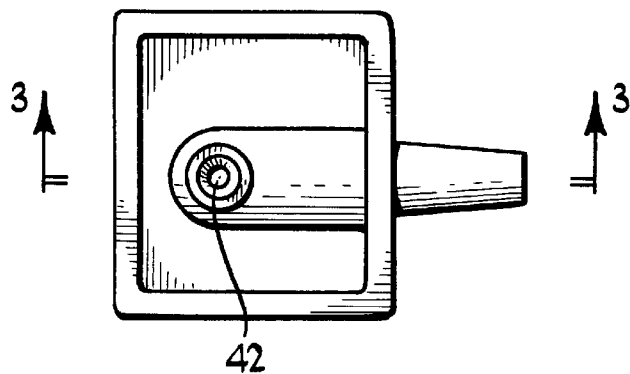
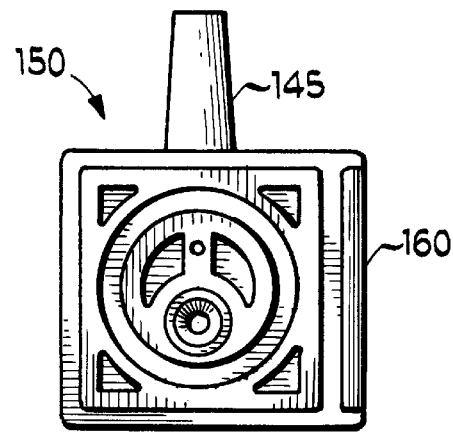
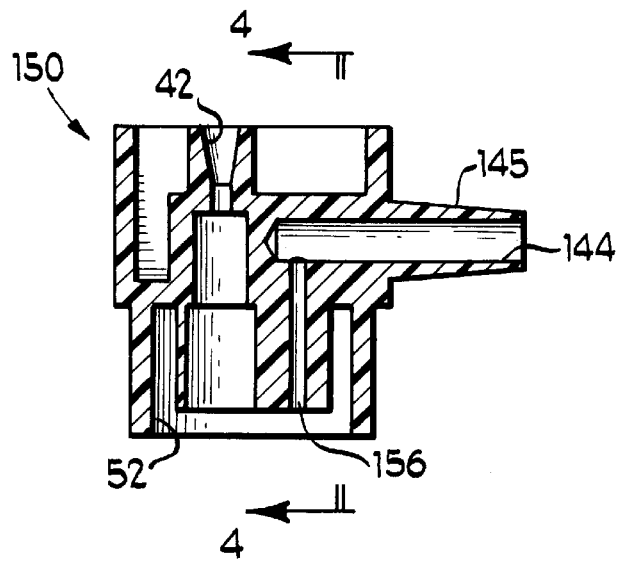
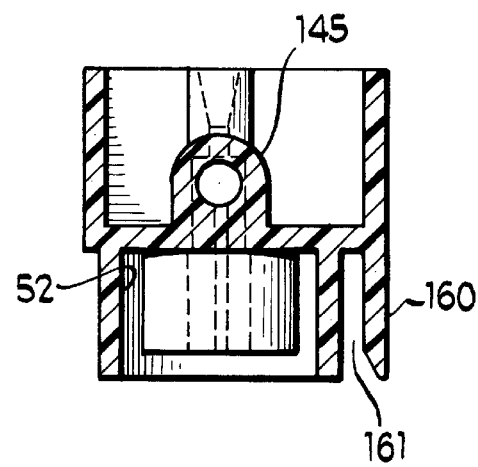

MECHANISM AND METHOD FOR MONITORING DUAL LUMEN BODY FLUID SUCTION SYSTEM

BACKGROUND OF THE INVENTION

Elongated slender and generally flexible drainage tubes commonly are axially inserted into body cavities for removal of fluid therefrom (liquid gastric secretions, gases, etc.). Generally, a suction/fluid collection system is connected to the proximal end of the drainage tube to facilitate drainage. In medical or hospital settings, a drainage tube might be inserted via the nasal passage or mouth through the esophagus to extend into the stomach or intestines, operable to retrieve unwanted fluid contents therefrom; and such a fluid drainage device is commonly known as a nasogastric tube.

The importance of continuous operation of an inserted drainage (or a nasoquastic) tube cannot be over estimated, such as in a patient who is obtunded, with intestinal obstruction, or is post-operative; as inadequate removal of unwanted gastric fluids can result in pneumonia, intestinal distention, morbidity, gastric wall trauma and bleeding, or even death.

One conventional form of dual lumen drainage tube 10 is illustrated in FIG. 1 herein, having a single exterior tube body 12 with wall structure that define dual lumens 14, 16 (or separated axially extended side-by-side passages). The passage 14 may branch off of the main body 12 via tubing 18 to a proximal end fitting 20 having at least one opening serving as inlet opening to the lumen 14. The passage 16 might extend to the proximal end of the main body, to a fitting 22 that presents outlet opening from lumen 16. The lumens 14, 16 are communicated together only via a small cross-over opening 24 in the tube wall structure at the distal tube end. The exterior tube wall adjacent its distal end has small holes 26 that open to the suction lumen 16. The lumen passages 14, 16 are of different cross-sectional areas: larger passage 16 serving as the suction or sump lumen and smaller passage 14 serving as the vent or makeup air lumen.

Suction/fluid collection system 28 (schematically illustrated only) can be connected via flexible transparent tubing 30 to the proximal end fitting 22 of the suction lumen. The opening in the makeup air lumen proximal end fitting 20 would be the atmospheric air, or could be contoured to accept a luer tip or the like for allowing easy connection via the inlet lumen 14 for syringe injection of fluids into the patient, or could provide for the connection of an antireflux valve (not shown).

After the distal end of the gastric tube 10 is axially inserted via the nose or mouth to position the side holes proximate the region within the patient to be drained, operation of the suction/fluid collection system 28 and reduced pressures in the suction lumen 16 would effectively withdraw proximate body fluids through the distal end tube side holes 26 and via the suction lumen 16 to the collection system; and the withdrawn fluids would also include atmospheric air inflowing via the makeup air vent lumen 14 and cross-over opening 24. This continuous air and retrieved body fluid flow via the drainage or suction lumen 16 helps prevent blockage of the distal tube end side holes and trauma to the stomach wall from excessive suction, while removing the body fluids as needed.

However, blockage of either the distal tube end side holes 26 or the suction lumen 16 by the retrieved fluid contents will result in reduced or total stoppage of proper fluid removal. Thus, close regular monitoring of continued drainage system operation is required.

Current methods of monitoring gastric tube function are subjective and imprecise. One presently used monitoring technique is visual, observing through the typically transparent suction tubing 30 the movement therein of the retrieved fluids flowing away from the drainage tube 10 and toward the suction/fluid collection system 28. This is not precise or reliable as: movement of a solidly filled tubing is difficult to perceive; the movement of fluid plugs might be slow or irregular; or a completely void tubing would be meaningless, as such could occur when there is no drainage flow (an acceptable situation) or when there is no air flow (not an acceptable situation). Also, detected fluid movement can be deceiving in that some minimal movement can occur in a poorly functioning tube. Another commonly used monitoring technique is audible, by having an attendant listen for whistling sounds of the makeup air flowing into the tubing opening of the makeup air lumen 14. However, proximate noises can make this detection effort difficult and/or insensitive; while it further requires the special time consuming individual services of an attendant.

OBJECTS AND SUMMARY OF THE INVENTION

This invention provides for improved monitoring of the operation of a body fluid dual lumen drainage system.

Basic objects of this invention are to provide apparatus and method for accurately, economically, easily and reliably monitoring a dual lumen drainage system (such as with a nasogastric tube.

Another object of this invention is to provide apparatus and method for monitoring a dual lumen drainage system that is simple, inexpensive, effective continuously, easily observed, and further can be incorporated into most conventionally used existing dual lumen body cavity drainage systems.

Another object of the invention is to route atmospheric air needed for venting a dual lumen medical drainage tube through a sealed transparent vessel partially filled with a safe transparent liquid, such as water, whereby resulting air flow is as bubbles rising through the vessel liquid, easily visible for offering assurance of proper functioning of the drainage tube.

BRIEF DESCRIPTION OF THE DRAWINGS

These and other objects, features or advantages of the invention will be more fully understood and appreciated after consideration of the following description of the invention, which includes as a part thereof the accompanying drawings, wherein:

FIG. 1 is a combination elevational/sectional view of an embodiment of the subject monitoring device, shown in a schematic hook-up with a conventional suction/fluid collection system and conventional dual lumen drainage device;

FIG. 2 is a top view of a preferred cap piece for a monitoring device similar to that illustrated in FIG. 1;

FIGS. 3 and 4 are sectional views of the cap piece, as taken respectively from line 3—3 in FIG. 2 and from line 4—4 in FIG. 3; and FIG. 5 is a bottom view of FIG. 4.

DETAILED DESCRIPTION OF THE INVENTION

The inventive monitoring device 38 is adapted to be connected in series with and upstream of the makeup or vent air lumen 14 of the drainage tube. The device is comprised as a vessel designed to hold liquid, the vessel being sealed other than having inlet and outlet openings 42, 44 respectively for forming the series flow hookup of atmospheric makeup air entering at inlet opening 42 and exiting at the outlet opening 44 via tubing 45 and fitting 47, and a press-fit connection relative to and with fitting 20 to the makeup air lumen 14.

The vessel is formed as a transparent open top tube 46 (somewhat as a common test tube) having a generally cylindrical side wall 48 blending into or terminating at a closed bottom end and an annular open top end; and a top piece or cap 50 seated sealingly over the open tube top end. An annular groove 52 in the underside of the top cap piece 50 can be provided for removably and sealingly receiving and holding the annular open tube top end, via a press-fit or threaded connection (not shown). An elongated tube 54 is press-fitted or otherwise seated and held in communication over the inlet opening 42, being extended downwardly almost to the tube bottom. The tube 54 might have many small orifices along it length but mostly near its bottom and/or a porous air-permeable plug 55 can be inserted into the lower outlet end of the tube 54, to define many fine outlet passages for air flow out the tube.

A check valve 56 in the top cap piece 50 can be provided for allowing gas discharge only out of the outlet opening 44. The check valve 56 can be comprised of an annular seat around internal top piece passageways 60 and 62 to the outlet opening 44, a ball 64 moveable vertically in the larger underside passageway 60 suited to close the passageways when biased upwardly against the seat and to open the passageways when lowered away from the seat, and a grate like screen 66 holding the ball in the passageway 60 while allowing the mentioned vertical ball movements. The check ball 64 would be made of material less dense than the tube liquid, to float in the liquid operable to block liquid migration out of the outlet opening 44; while otherwise when in the air only, the check ball 64 would be gravity biased to the check valve 56 open position (as shown). The screen 66 might also serve to break up bubbles, for minimizing water migration to the air lumen 14.

The tube 46 is designed to be filled with water or other suitable preferably transparent safe liquid to a level 68 somewhat as indicated, between markings 70 and 72 on the tube wall corresponding to the "FULL" and "FILL" liquid levels. As such, the porous air-permeable plug 55 and lower tube end are positioned under the contained vessel liquid, while check valve outlet 56 from the vessel is spaced above or overlying the vessel liquid. Makeup air flow via the inlet opening 42, through the vessel, and out of the outlet opening 44 thus must occur as visible bubbles 74 rising through the liquid, such bubbles being easily, reliably and remotely detected and/or viewed by an attendant for indicating concurrent and continuous makeup air flow through the vent lumen 14 and consequently continued operation of the drainage system. The regularity of and/or changing the bubble pattern generated can be compared by the attendant over repeated observations to evaluate the consistency over time of the makeup air flow.

The top piece or cap 150 illustrated in FIGS. 2–5 has minor changes from the cap 50 in FIG. 1. For example, the outlet opening 144 is comprised as a male fitting 145 suited to have the tubing 45 positioned thereon in forming the air-tight passageway for makeup air flow to the vent lumen 14. Further, the check valve 56 is eliminated, and instead a through bore 156 is defined between the underside of the cap and the outlet fitting opening 144, the bore being large enough in size for accommodating sufficient makeup air flow but small enough to restrict excessive free flow of liquid, or spillage, into the tubing 45. Also, the exterior shape of the top cap piece 150 might be square, with a hook or tab 160 downwardly projecting along a side edge adjacent the fitting 145 and defining a recess 161, suited for hanging the cap 150 and connected tube (not shown but like tube 46 for defining the monitoring device) onto an appropriate support structure (not shown), with the tube being oriented along a substantially vertical axis.

The tube 48, top cap piece 50 or 150, and screen 66 might be made of a rigid PVC or other stable plastic; while the check ball 64 might be made of a polypropylene. Tubing can be of conventional medical care materials.

Although specific embodiments have been illustrated and discussed, minor changes could be made without departing from the inventive teaching. Accordingly, the invention is to determined by the scope of the following claims.

What is claimed is:

1. Apparatus for monitoring operation of a medical drainage system comprised of a dual lumen tube having linked suction and vent lumens, and a suction/collection system connected to the suction lumen operable to draw a vacuum from the suction lumen with resulting makeup air flow through the vent lumen linked serially upstream from the suction lumens comprising the combination of a dual lumen tube having a vent lumen and a suction lumen, a sealed vessel adapted to be partially filled with a liquid, the vessel having a substantially fixed area inlet configured to open directly between the atmosphere and the vessel under and into the vessel liquid, the vessel also having an outlet that is located above the vessel liquid, and means for connecting the vessel outlet in series with and upstream of the vent lumen of the drainage tube, wherein negative pressures applied to the suction lumen under proper drainage tube operation and resulting makeup air flow through the vent lumen will create makeup atmospheric air flow bubbles rising through the vessel liquid, and means for detecting the rising bubbles for monitoring operation of the drainage tube.

2. Monitoring apparatus according to claim 1, further comprising the vessel having a transparent vertically extended exterior wall adjacent the rising bubbles whereby the means for detecting the rising bubbles is visual by a nearby attendant.

3. Monitoring apparatus according to claim 2, further comprising the transparent exterior vessel wall being in the form of a cylinder, whereby a nearby attendant can see the rising bubbles from all sides of the vessel.

4. Monitoring apparatus according to claim 1, further comprising anti-spill means in the vessel between the normal liquid surface and vessel outlet operable for restricting free exiting of water from the vessel outlet.

5. Monitoring apparatus according to claim 1, further comprising the vessel having a transparent vertically extended exterior wall adjacent the rising bubbles whereby the means for detecting the rising bubbles is visual by a nearby attendant, and anti-spill means in the vessel between the normal liquid surface and vessel outlet operable for restricting free exiting of water from the vessel outlet.

6. Monitoring apparatus according to claim 1, further comprising the vessel having a transparent vertically extended cylindrical exterior wall adjacent the rising bubbles whereby the means for detecting the rising bubbles is visual by a nearby attendant from all sides of the vessel, and anti-spill means in the vessel between the normal liquid surface and vessel outlet operable for restricting free exiting of water from the vessel outlet.

7. A method for monitoring operation of a medical drainage system comprised of a dual lumen having linked suction and vent lumens, and a suction/collection system connected to the suction lumen operable to draw a vacuum from the suction lumen with resulting makeup air flow through the vent lumen linked serially upstream from the suction lumen, comprising the steps of routing the makeup air for the vent lumen of the drainage tube initially through a sealed transparent vessel connected in series with and upstream of the vent lumen, and visually observing the flow of makeup air through the vessel as visible bubbles rising through the vessel liquid from an air inlet entering under and into the vessel liquid and before the air exits from an air outlet spaced above the vessel liquid and flows then through the vent lumen and the serially upstream linked suction lumen to the suction/collection system.

8. A method for monitoring operation of a medical drainage system comprised of a dual lumen having linked suction and vent lumens, and a suction/collection system connected to the suction lumen operable to draw a vacuum from the suction lumen with resulting makeup air flow through the vent lumen linked serially upstream from the suction lumen, comprising the steps of routing the makeup air for the vent lumen of the drainage tube initially through a vessel connected in series with and upstream of the vent lumen, and detecting the makeup air flowing through the vessel as bubbles rising through the vessel liquid from an air inlet entering under and into the vessel liquid and before the air exits from an air outlet spaced above the vessel liquid and flows then through the vent lumen and the serially upstream linked suction lumen to the suction/collection system.

* * * * *